US012302927B2

(12) United States Patent
Peng et al.

(10) Patent No.: US 12,302,927 B2
(45) Date of Patent: *May 20, 2025

(54) APPLICATION OF ASPARTIC ACID DERIVATIVE IN PREPARING ANIMAL FEED ADDITIVE

(71) Applicant: ANIPHA TECHNOLOGIES PTY LTD, Toorak Gardens (AU)

(72) Inventors: Xianfeng Peng, Guangzhou (CN); Huacheng Huang, Guangzhou (CN)

(73) Assignee: ANIPHA TECHNOLOGIES PTY LTD, Toorak Gardens (AU)

( * ) Notice: Subject to any disclaimer, the term of this patent is extended or adjusted under 35 U.S.C. 154(b) by 768 days.

This patent is subject to a terminal disclaimer.

(21) Appl. No.: 17/290,257

(22) PCT Filed: Nov. 5, 2018

(86) PCT No.: PCT/CN2018/113906
§ 371 (c)(1),
(2) Date: Apr. 30, 2021

(87) PCT Pub. No.: WO2020/093187
PCT Pub. Date: May 14, 2020

(65) Prior Publication Data
US 2022/0015393 A1    Jan. 20, 2022

(51) Int. Cl.
| | | |
|---|---|---|
| *A23K 20/142* | (2016.01) | |
| *A23K 50/30* | (2016.01) | |
| *A23K 50/60* | (2016.01) | |
| *A23K 50/75* | (2016.01) | |
| *A23K 50/80* | (2016.01) | |
| *A61K 31/197* | (2006.01) | |
| *C07C 229/24* | (2006.01) | |
| *C07C 237/12* | (2006.01) | |
| *C07C 275/16* | (2006.01) | |

(52) U.S. Cl.
CPC .......... *A23K 20/142* (2016.05); *A23K 50/30* (2016.05); *A23K 50/60* (2016.05); *A23K 50/75* (2016.05); *A23K 50/80* (2016.05); *A61K 31/197* (2013.01); *C07C 229/24* (2013.01); *C07C 237/12* (2013.01); *C07C 275/16* (2013.01)

(58) Field of Classification Search
CPC ...... A23K 20/142; A23K 50/30; A23K 50/60; A23K 50/75; A23K 50/80; A23K 20/24; A23K 10/30; A23K 10/37; A23K 20/105; A23K 20/147; A23K 20/158; A23K 20/163; A23K 20/195; A23K 20/20; A23K 20/28; A23K 20/30; A23K 50/40; A23K 10/16; A23K 20/174; A23K 50/00; A61K 31/197; C07C 229/24; C07C 237/12; C07C 275/16; C07K 5/06026
See application file for complete search history.

(56) References Cited

U.S. PATENT DOCUMENTS

| | | | |
|---|---|---|---|
| 2003/0096741 A1 | 5/2003 | Slattery | |
| 2013/0018102 A1* | 1/2013 | Dente, III | ............... A23L 33/10 |
| | | | 514/574 |

FOREIGN PATENT DOCUMENTS

| | | | |
|---|---|---|---|
| EP | 0029000 A1 | 5/1981 | |
| JP | S58175452 A | 10/1983 | |
| WO | WO-2020093188 A1 * | 5/2020 | ............. A23K 10/30 |

OTHER PUBLICATIONS

Isidro-Llobet et. al. (2009), Amino Acid-Protecting Groups, Chem. Rev., 109, 2455-2504 (Year: 2009).*
Espacenet Patent Translation Spec (WO2020093188A1) (Year: 2018).*
Delgado et. al. (2013), Synthesis, Crystal and Molecular Structure, and Hydrogen-bonding Patterns in Hydantoin-L-Aspartic Acid, Avences in Quimica, 8, 59-63 (Year: 2013).*
Rezaei et. al. ((2013), Biochemical and physiological bases for utilization of dietary amino acids by young Pigs, Journal of Animal Science and Biotechnology, 4, 1-12 (Year: 2013).*
Patani et. al. ((1996) Bioisosterism a rational approach in drug design, Chem. Rev., 96, 3147-3176). (Year: 1996).*
International Search Report of PCT/CN2018/113906, dated Jun. 27, 2019.
English Translation of International Search Report of PCT/CN2018/113906.

(Continued)

*Primary Examiner* — Juliet C Switzer
*Assistant Examiner* — Dawanna Shar-Day White
(74) *Attorney, Agent, or Firm* — Kam Wah Law

(57) ABSTRACT

Disclosed is use of an aspartic acid derivative having a structure represented by formula (I), or a racemate, stereoisomer, geometric isomer, tautomer, solvate or feed-acceptable salt thereof, in preparing an animal feed additive that significantly improves production performance of farmed animals,

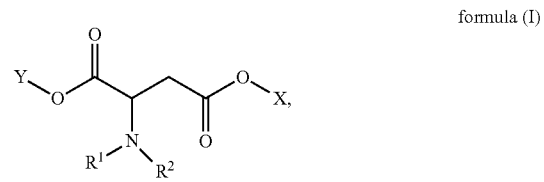

formula (I)

wherein Y and X are independently selected from a $C_1$-$C_{20}$ alkyl or —H; $R^1$ is $R^{1a}C(=O)$ or H; $R^2$ is $R^{2a}C(=O)$; and the $R^{1a}$ and $R^{2a}$ are independently selected from (A)(B)N—$(CH_2)_{0-5}$—, and the A and B are independently selected from a $C_1$-$C_{20}$ alkyl or —H.

15 Claims, No Drawings

(56) References Cited

OTHER PUBLICATIONS

Wu, Fan, "Multi-functional Novel Feed Additives—Bioactive Peptides," Veterinary Pharmaceuticals & Feed Additives, vol. 13, No. 3, Dec. 31, 2008 (Dec. 31, 2008).
Lin, Fanping, "Development and Utilization of Bioactive Peptides in Foods and Feed Industry," Fujian Journal of Animal Husbandry, vol. 22, No. 2, Dec. 31, 2000 (Dec. 31, 2000).
Randall K. Johnson, "Reversal of toxicity and antitumor activity of N-(phosphonacetyl)-L-aspartate by uridine or carbamyl-DLaspartate," Biochemical Pharmacology, vol. 26, Issue 1, pp. 81-84, Jan. 1, 1977(Jan. 1, 1977).
G. S. Jagannatha Rao, "N-Carbamoyl-DL-aspartic acid," Acta Crystallographica, B38, pp. 1672-1674, 1982.
Gerzon E. Delgado, "Synthesis, crystal and molecular structure, and hydrogen-bonding patterns in hydantoin-L-aspartic acid," Avances en Quimica, vol. 8, Issue 2, pp. 59-63, 2013.
English Translation of EP0029000A1.
English Translation of Wu, Fan, "Multi-functional Novel Feed Additives-Bioactive Peptides," Veterinary Pharmaceuticals & Feed Additives, vol. 13, No. 3, Dec. 31, 2008 (Dec. 31, 2008).
English Translation of Lin, Fanping, "Development and Utilization of Bioactive Peptides in Foods and Feed Industry," Fujian Journal of Animal Husbandry, vol. 22, No. 2, Dec. 31, 2000 (Dec. 31, 2000).
Jielin Duan, "Dietary supplementation with L-glutamate and L aspartate alleviates oxidative stress in weaned piglets challenged with hydrogen peroxide", Amino Acids, vol. 48, No. 53-64, Aug. 9, 2015.
English Translation of JPS58175452A.
Extended European Search Report of EP3868775 (Oct. 6, 2021).
Japanese Examination Report of JP2021524335A (Aug. 7, 2022).

\* cited by examiner

APPLICATION OF ASPARTIC ACID DERIVATIVE IN PREPARING ANIMAL FEED ADDITIVE

CROSS REFERENCE TO RELATED APPLICATION

This is a U.S. national stage application of the International Patent Application No. PCT/CN2018/113906, filed Nov. 5, 2018, which is incorporated herein by reference in its entirety.

TECHNICAL FIELD

The present invention relates to the field of animal feed additives, and particularly relates to a use of an aspartic acid derivative in preparing an animal feed additive, a feed composition containing an aspartic acid derivative and use thereof in preparing animal feed additives and animal feeds.

BACKGROUND

N-carbamoyl aspartic acid is an endogenous product in animals. It is unstable in vitro when exposed to acid and can be hydantoinated to form a cyclic urea substance. It can be used as an intermediate for the preparation of orotic acid in the field of chemical fine chemical. N-carbamoyl aspartic acid is one of the ingredients of cosmetics, which has the effect of whitening and nourishing the skin. It can also function as an absorptive carrier in the preparation of dipeptide drugs to promote the absorption of dipeptide drugs.

SUMMARY

The present invention provides use of N-carbamoyl aspartic acid and its derivative (which two are collectively referred to as aspartic acid derivatives hereinafter), or a racemate, stereoisomer, geometric isomer, tautomer, solvate and feed-acceptable salt thereof, in preparing an animal feed additive. The present invention further provides a feed composition containing the aspartic acid derivative or the racemate, stereoisomer, geometric isomer, tautomer, solvate and feed-acceptable salt thereof, and use of the composition in preparing animal feed additives and animal feeds.

In one aspect, the present invention provides an aspartic acid derivative having a structure represented by formula (I),

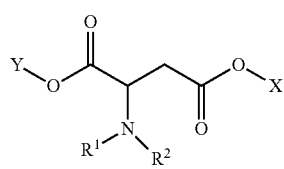

formula (I)

In some technical solutions, $R^1$ is $R^{1a}C(\!=\!O)\!-\!$ or $-\!H$, and $R^2$ is $R^{2a}C(\!=\!O)\!-\!$; the $R^{1a}$ and $R^{2a}$ are $(A)(B)N\!-\!(CH_2)_{0\text{-}5}\!-\!$ independently; the A and B are independently selected from a $C_1\text{-}C_{20}$ alkyl or $-\!H$; and Y and X are independently selected from a $C_1\text{-}C_{20}$ alkyl or $-\!H$.

In some technical solutions, $R^1$ in the aspartic acid derivative is $-\!H$.

In some technical solutions, A and B in the aspartic acid derivative are $-\!H$ at the same time.

In some technical solutions, Y and X in the aspartic acid derivative are $-\!H$.

In some technical solutions, Y and X in the aspartic acid derivative are independently selected from a $C_1\text{-}C_{20}$ alkyl or $-\!H$, and are not $-\!H$ at the same time.

In some technical solutions, Y and X in the aspartic acid derivative are independently selected from a $C_1\text{-}C_4$ alkyl or $-\!H$, and are not $-\!H$ at the same time.

In some technical solutions, the feed-acceptable salt of the aspartic acid derivative is a metal ion salt.

In some technical solutions, the feed-acceptable salt of the aspartic acid derivative is preferably a sodium ion salt, a zinc ion salt, a copper ion salt, an iron ion salt, or a calcium ion salt.

In another aspect, the present invention further provides use of the aspartic acid derivative or the racemate, stereoisomer, geometric isomer, tautomer, solvate and feed-acceptable salt thereof provided in the present invention in preparing animal feed additives and animal feeds.

In another aspect, the present invention provides a feed composition, containing at least one of the aspartic acid derivative or the racemate, stereoisomer, geometric isomer, tautomer, solvate and feed-acceptable salt thereof provided in the present invention, and at least one auxiliary material usable for feed.

The auxiliary material usable for feed is a carrier, a diluent, an excipient, a medium, or a combination thereof that is usable for feed.

In some technical solutions, the feed composition further contains animal feed raw materials.

In some technical solutions, the feed composition further contains an additional animal feed additive.

In some technical solutions, the feed composition further contains animal feed raw materials and an additional animal feed additive.

In some technical solutions, the additional animal feed additive can be selected from a nutritional feed additive and/or a general feed additive and/or a medicinal feed additive.

In another aspect, the present invention provides use of the feed composition in preparing animal feed additives.

In another aspect, the present invention provides use of the feed composition in preparing animal feeds.

In another aspect, the present invention further provides a method for improving production performance of a farmed animal.

The present invention has the following beneficial effects.

The results of animal breeding experiments show that the aspartic acid derivative or the racemate, stereoisomer, geometric isomer, tautomer, solvate and feed-acceptable salt thereof provided in the present invention can be used as an animal feed additive, and has a good effect of improving production performance of a farmed animal.

Any embodiment of any aspect of the present invention can be combined with other embodiments as long as there is no contradiction between them. In addition, any technical feature in any embodiment of any aspect of the present invention can apply to said technical feature in other embodiments, as long as there is no contradiction between them.

The above descriptions are merely an overview of some aspects of the present invention, but the present invention is not limited to these aspects. Contents involved in the above descriptions and contents of other aspects will be described in more detail and more thoroughly below.

A further detailed description of the present invention is given below.

Now some embodiments of the present invention will be described in detail, examples of which will be illustrated by the accompanying structural formulas and chemical formulas. The present invention is intended to cover all alternatives, modifications and equivalent technical solutions, which are all included in the scope of the present invention as defined by the claims. In addition, for purpose of clarity, some technical features of the present invention are described separately in multiple independent embodiments, but they can also be provided in combination or provided in any suitable sub-combination in a single embodiment.

Compounds.

The compound involved in the present invention is an aspartic acid derivative having a structure represented by formula (I),

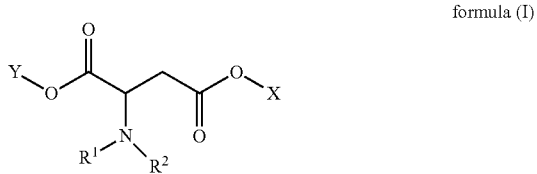

formula (I)

wherein Y and X are substituent groups on the oxygen atom (abbreviated as O) where the active hydrogen on the carboxyl group of aspartic acid is substituted, and $R^1$ and $R^2$ are substituent groups on the nitrogen atom (abbreviated as N). Y and X are independently selected from a $C_1$-$C_{20}$ alkyl or —H; $R^1$ is $R^{1a}C(=O)$— or —H; $R^2$ is $R^{2a}C(=O)$—; the $R^{1a}$ and $R^{2a}$ are independently selected from (A)(B)N—$(CH_2)_{0-5}$—; the A and B are independently selected from a $C_1$-$C_{20}$ alkyl or —H.

Generally, "substituted" means that one or more hydrogen atoms that can be substituted in a given structure are substituted by specific substituents. A substituted group may have a substituent group to substitute at each position that can be substituted in the group. When more than one position in the given structural formula can be substituted by one or more substituent groups of a specific group, the each positions may be substituted by the substituent groups identically or differently.

In the present invention, "$C_1$-$C_{20}$ alkyl" represents a saturated alkyl containing 1 to 20 carbon atoms, such as methyl, ethyl, propyl, isopropyl, . . . , a straight or branched chain alkyl containing 20 carbon atoms; "$(CH_2)_{0-5}$" represents containing 0 to 5 methylenes; and "(A)(B)N" represents an amino group in which hydrogen atoms are substituted by a substituent group A and a substituent group B.

Optionally, $R^1$ is $R^{1a}C(=O)$—; $R^2$ is $R^{2a}C(=O)$—; the $R^{1a}$ and $R^{2a}$ are independently selected from (A)(B)N—$(CH_2)_{0-5}$—; and the A and B are independently selected from a $C_1$-$C_{20}$ alkyl or —H.

Optionally, $R^1$ is —H; $R^2$ is $R^{2ao}$ C. (=O)—, and $R^{2a}$ is (A)(B)N—$(CH_2)_{0-5}$—; and the A and B are independently selected from a $C_1$-$C_{20}$ alkyl or —H.

Optionally, when A and B in the (A)(B)N—$(CH_2)_{0-5}$— are —H at the same time, (A)(B)N—$(CH_2)_{0-5}$— is $NH_2$—$(CH_2)_{0-5}$—.

Optionally, A and B in the (A)(B)N—$(CH_2)_{0-5}$— are independently selected from a $C_1$-$C_{20}$ alkyl or —H, and are not —H at the same time.

Further, $R^{2a}$ is (A)(B)N—$(CH_2)_{0-5}$—, the A and B are each a $C_1$-$C_{20}$ alkyl.

Still further, $R^{2a}$ is (A)(B)N—$(CH_2)_{0-5}$—, the A and B are each a $C_1$-$C_4$ alkyl.

Specifically, the $R^{2a}$ is (A)(B)N—$(CH_2)_{0-5}$—, the A and B are each a straight chain $C_1$-$C_4$ alkyl.

In some embodiments, $R^{2a}$ is $(CH_3)_2N$—, (N,N'-dimethyl)N—$(CH_2)$—, $R^{2a}$ (N,N'-dimethyl)N—$(CH_2)_2$—, (N,N'-dimethyl)N—$(CH_2)_3$—, (N,N'-dimethyl)N—$(CH_2)_4$—, or (N,N'-dimethyl)N—$(CH_2)_5$—.

In some other embodiments, $R^{2a}$ is N,N'-di-n-butylamino, (N,N'-di-n-butyl)N—$(CH_2)$—, (N,N'-dibutylmethyl)N—$(CH_2)_2$—, (N,N'-di-n-butylmethyl)N—$(CH_2)_3$—, (N,N'-di-n-butyl methyl)N—$(CH_2)_4$—, or (N,N'-di-n-butyl methyl)N—$(CH_2)_5$—.

Specifically, the $R^{2a}$ is (A)(B)N—$(CH_2)_{0-5}$—, the A and B are each a branched chain $C_1$-$C_4$ alkyl.

In some embodiments, $R^{2a}$ is N,N'-diisopropylamino, (N,N'-diisopropyl)N—$(CH_2)$—, (N,N'-diisopropyl)N—$(CH_2)_2$—, (N,N'-diisopropyl)N—$(CH_2)_3$—, (N,N'-diisopropyl)N—$(CH_2)_4$—, or (N,N'-diisopropyl)N—$(CH_2)_5$—.

In some other embodiments, $R^{2a}$ is N,N'-diisobutylamino, (N,N'-diisobutyl)N—$(CH_2)$—, (N,N'-diisobutyl)N—$(CH_2)_2$—, (N,N'-diisobutyl)N—$(CH_2)_3$—, (N,N'-diisobutyl)N—$(CH_2)_4$—, or N,N'-diisobutyl)N—$(CH_2)_5$—.

Further, $R^{2a}$ is (A)(B)N—$(CH_2)_{0-5}$—, the A is a $C_1$-$C_{20}$ alkyl, and B is H at the same time. Still further, $R^{2a}$ is (A)(B)N—$(CH_2)_{0-5}$—, the A is a $C_1$-$C_4$ alkyl, and B is H at the same time.

Specifically, $R^{2a}$ is (A)(B)N—$(CH_2)_{0-5}$—, the A is a straight chain $C_1$-$C_4$ alkyl, and B is H at the same time.

In some embodiments, $R^{2a}$ is N-methylamino, (N'-1H-N-methyl)N—$(CH_2)$—, (N'-1H-N-methyl)N—$(CH_2)_2$—, (N'-1H-N-methyl)N—$(CH_2)_3$—, (N'-1H-N-methyl)N—$(CH_2)_4$—, or (N'-1H-N-methyl)N—$(CH_2)_5$—.

In some other embodiments, $R^{2a}$ is N-n-butylamino, (N'-1H-N-n-butyl)N—$(CH_2)$—, (N'-1H-N-n-butyl)N—$(CH_2)_2$—, (N'-1H-N-n-butyl)N—$(CH_2)_3$—, (N'-1H-N-n-butyl)N—$(CH_2)_4$—, or (N'-1H-N-n-butyl)N—$(CH_2)_5$—.

Specifically, $R^{2a}$ is (A)(B)N—$(CH_2)_{0-5}$—, the A is a branched chain $C_1$-$C_4$ alkyl, and B is H at the same time.

In some embodiments, $R^{2a}$ is N-isopropylamino, (N'-1H-N-isopropyl)N—$(CH_2)$—, (N'-1H-N-isopropyl)N—$(CH_2)_2$—, (N'-1H-N-isopropyl)N—$(CH_2)_3$—, (N'-1H-N-isopropyl)N—$(CH_2)_4$—, or (N'-1H-N-isopropyl)N—$(CH_2)_5$—.

In some other embodiments, $R^{2a}$ is N-isobutylamino, (N'-1H-N-isobutyl)N—$(CH_2)$—, (N'-1H-N-isobutyl)N—$(CH_2)_2$—, (N'-1H-N-isobutyl)N—$(CH_2)_3$—, (N'-1H-N-isobutyl)N—$(CH_2)_4$—, or (N'-1H-N-isobutyl)N—$(CH_2)_5$—.

Optionally, Y and X are —H at the same time.

Optionally, Y and X are independently selected from a $C_1$-$C_{20}$ alkyl or —H, and are not —H at the same time.

Specifically, Y and X are each a $C_1$-$C_{20}$ alkyl at the same time or are respectively one of a $C_1$-$C_{20}$ alkyl and —H.

Optionally, the $C_1$-$C_{20}$ alkyl is a straight chain alkyl.

In some embodiments, the straight chain alkyl is methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, or n-octadecyl.

Optionally, the $C_1$-$C_{20}$ alkyl is a branched chain alkyl.

In some embodiments, the branched chain alkyl is isopropyl or tert-butyl. Optionally, the $C_1$-$C_{20}$ alkyl is a cycloalkyl.

In some embodiments, the cycloalkyl is cyclopropyl, cyclopentyl, or cyclohexyl.

In some embodiments, the aspartic acid derivative having the structure represented by formula (I) is a feed-acceptable salt.

Further, the feed-acceptable salt is a metal ion salt, and the metal ion salt is a substance formed by bonding of a metal ion to the aspartic acid derivative as an acid donor following the principle of conservation of charge, where a metal ion bond may be complexed with the aspartic acid derivative or a metal ion may be chelate-bonded to the aspartic acid derivative by means of the electrical properties of the metal ion(s) to form a chelate compound.

Optionally, the metal ion is a monovalent metal ion, a divalent metal ion, or a trivalent metal ion.

Specifically, the monovalent metal ion includes, but not limited to, sodium ion, potassium ion, lithium ion, and ammonium ion; the divalent metal ion includes, but not limited to, calcium ion, magnesium ion, zinc ion, copper ion, ferrous ion, and manganese ion; the trivalent metal ion includes, but not limited to, iron ion, nickel ion, chromium ion, and aluminum ion.

In some embodiments, the metal ion is zinc ion.
In some other embodiments, the metal ion is copper ion.
In some other embodiments, the metal ion is sodium ion.
In some other embodiments, the metal ion is calcium ion.
In some other embodiments, the metal ion is iron ion.

Preparation and Purification of Compounds.

A method for preparing the aspartic acid derivative having the structure represented by formula (I) involved in the present invention uses aspartic acid (Asp) as a starting raw material, and chemical reactions involved mainly include acylation of amino groups, esterification of carboxyl groups and hydrolysis of carboxyl esters.

In some embodiments, Y and X in formula (I) are each a $C_1$-$C_{20}$ alkyl or H but are not H at the same time, and the method for preparing the aspartic acid derivative represented by formula (I) includes two reaction phases: the esterification of carboxyl groups and the acylation of amino groups, as shown in formula (II).

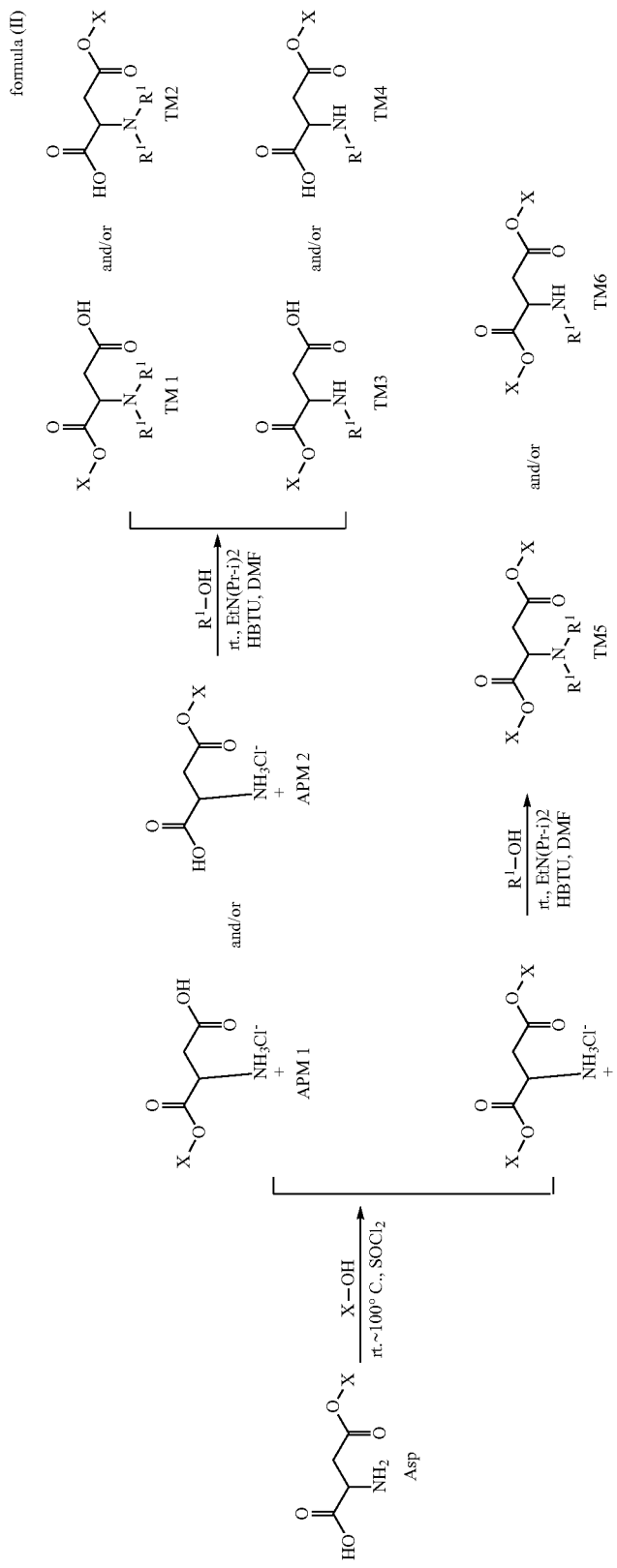

It is to be noted that X and $R^1$ in formula (II) only represent substituent groups, and if the substance represented by the raw materials X—OH and $R^1$—OH is not a single substance, X or $R^1$ should be understood as a collection of substituent groups; in formula (II) and the following formulas, when $R^1$—OH is $H_2N$—$(CH_2)_{0-5}$(C=O)OH, the amino group contained is protected by a protective group tert-butoxycarbonyl (Boc-), and after the reaction, the protective group Boc is removed under trifluoroacetic acid ($F_3CCOOH$) or other conditions for substituent removal; in addition, $SOCl_2$ is thionyl chloride, rt. stands for room temperature, $EtN(Pr-i)_2$ stands for diisopropylethylamine, DMF stands for N,N-dimethylformamide, and HBTU stands for O-benzotriazole-tetramethyluronium hexafluorophosphate (coupling agent).

In some embodiments, Y and X are —H at the same time, and a method for synthesizing the aspartic acid derivative uses di-tert-butyl aspartate (t-Bu-Asp) as a raw material, as shown in formula (III).

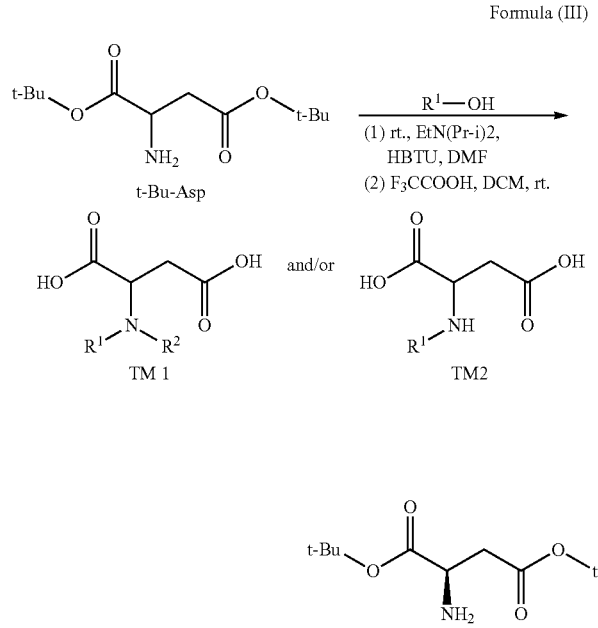

Formula (III)

It is to be noted that $R^1$ in formula (III) only represents a substituent group; when the substance represented by the raw material $R^1$—OH is not a single substance, $R^1$ on the target material (TM) should be understood as a collection of substituent groups; and t-Bu stands for tert-butyl as the protective group for the carboxyl, DCM stands for dichloromethane, NaOH stands for sodium hydroxide, and $F_3CCOOH$ stands for trifluoroacetic acid.

Further, when Y and X are —H at the same time or are respectively one of $C_1$-$C_{20}$ alkyl and —H, the aspartic acid derivative reacts with metal chloride or metal bromide under alkaline conditions to form a metal ion salt of the aspartic acid derivative, such as zinc salt, copper salt, calcium salt, iron salt, sodium salt, or other metal ion salt involved in the present invention.

In some embodiments, the di-tert-butyl aspartate is a chiral compound, and the di-tert-butyl aspartate of the present invention is selected from levorotatory di-tert-butyl L-(−)-aspartate (having a structure represented by formula (IV)), dextrorotatory di-tert-butyl D-(+)-aspartate (having a structure represented by formula (V)), or racemate di-tert-butyl DL-(±)-aspartate, which reacts with alcohol and carboxylic acid derivatives involved to obtain a stereoisomer or racemate of the aspartic acid derivative with a chiral center.

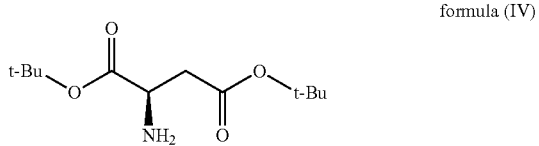

formula (IV)

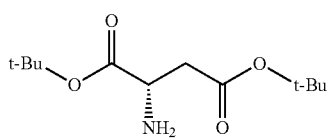

formula (V)

In some embodiments, the chiral stereoisomers of di-tert-butyl aspartate and the stereoisomers of the aspartic acid derivative can undergo stereo configuration conversion under suitable conditions, such as the three-dimensional conformational interconversion of t-Bu-aspartic acid or the aspartic acid derivative. For example, the three-dimensional conformational interconversion process of t-Bu-aspartic acid is as shown in formula (VI):

formula (VI)

When the involved reactant reacts with di-tert-butyl aspartate and the like to produce a corresponding aspartic acid derivative with a rigid structure, the reaction substrate can generate different geometric isomer products during the reaction.

The aforementioned stereoisomers, geometric isomers, and tautomers are also included in the scope of the present invention.

The term "stereoisomers" refers to the compounds having the same chemical structure but different arrangements of atoms or groups in space, including enantiomers, diastereomers, conformational isomers, geometric isomers, atropisomers, etc. The term "enantiomers" refers to two isomers of a compound that are mirror images of each other but are non-superposable. The term "diastereomers" refers to stereoisomers that have two or more chiral centers and whose molecules are not mirror images of each other, with different physical properties such as melting points, boiling points, spectral properties, and reactivity. Mixtures of diastereomers can be separated by high-resolution analysis operations such as electrophoresis or chromatography. The term "tautomers" refers to structural isomers with different energies that can be converted into each other through a low energy barrier.

In some embodiments, the process for preparing the aspartic acid derivative provided in the present invention also involves the separation, purification or recrystallization process of the reaction product. The reaction product can be obtained as a crude product from the reaction system by the solvent removal method. In order to obtain solid substances with higher chemical purity and lower impurity content, the crude product is dissolved, crystallized or precipitated or recrystallized and separated in alcohol solvents, alcohol-water mixed solvents or other organic solvents that can be used for product recrystallization under suitable temperature, light and mechanical vibration conditions, to obtain an aspartic acid derivative with a certain crystal state. The aspartic acid derivative with a certain crystal state is an aspartic acid derivative crystal or a solvate of the aspartic acid derivative. The solvate of the aspartic acid derivative can be selected from a hydrate of the aspartic acid derivative or an ethanolate of the aspartic acid derivative.

The term "solvate" refers to an co-crystallizing complex formed by bonding of the compound of the present invention to chemically equivalent or non-chemically equivalent solvent molecules through non-covalent intermolecular forces due to external conditions and internal conditions during the process of contact with solvent molecules. Solvents that form solvates include, but are not limited to, water, acetone, ethanol, methanol, dimethyl sulfoxide, ethyl acetate, acetic acid, isopropanol, etc. The term "hydrate" refers to an complex or crystal formed when the solvent molecules are water, that is, a compound obtained by bonding of chemically equivalent or non-chemically equivalent water through non-covalent intermolecular forces.

In order to obtain solid substances with higher chemical purity and lower impurity content, the preparation of the aspartic acid derivative provided in the present invention can also be processed by the salting-out method. The salting-out method is a process of using the principle of acid-base neutralization method, acid-base coordination method, or acid-base chelation method to make the aspartic acid derivative and the corresponding organic base, inorganic base, organic acid, or inorganic acid salt precipitate to obtain a feed-acceptable salt.

The feed-acceptable salt is a salt formed by the aspartic acid derivative of the present invention and an organic base, an inorganic base, an organic acid, or an inorganic acid that is non-toxic to animals. The "feed-acceptable" means that the substance or composition must be suitable in terms of chemistry or toxicology, and is related to the feed formed thereof or the farmed animals.

In some embodiments, the aspartic acid derivative is a diester or mixed ester (that is, Y and X are identical or different $C_1$-$C_{20}$ alkyl at the same time), which, in the salting-out precipitation process of post-treatment, forms an acid-base coordination salt and/or acid-base chelated salt with an inorganic acid or an organic acid. The organic acid includes, but not limited to, acetate, maleate, succinate, mandelate, fumarate, malonate, malate, 2-hydroxypropionate, pyruvate, oxalate, glycolate, salicylate, glucuronate, galactitolate, citrate, tartrate, aspartate, glutamate, benzoate, p-methylbenzoate, cinnamate, p-toluenesulfonate, benzenesulfonate, methanesulfonate, ethanesulfonate, trifluoromethanesulfonate, or a combination thereof. The inorganic acid includes, but not limited to, hydrochloride, hydrobromide, phosphate, sulfate, nitrate, or a combination thereof.

In some embodiments, the aspartic acid derivative is a monoester (that is, Y and X are respectively one of a $C_1$-$C_{20}$ alkyl and —H), which, in the salting-out precipitation process of post-treatment, forms an acid-base coordination salt and/or acid-base chelated salt with an organic acid or an inorganic acid, or forms an acid salt with an organic base or an inorganic base. The organic acid includes, but not limited to, acetate, maleate, succinate, mandelate, fumarate, malonate, malate, 2-hydroxypropionate, pyruvate, oxalate, glycolate, salicylate, glucuronate, galactitolate, citrate, tartrate, aspartate, glutamate, benzoate, p-methylbenzoate, cinnamate, p-toluenesulfonate, benzenesulfonate, methanesulfonate, ethanesulfonate, trifluoromethanesulfonate, or a combination thereof. The inorganic acid includes, but not limited to, hydrochloride, hydrobromide, phosphate, sulfate, nitrate, or a combination thereof. The organic base includes, but not limited to, ammonia or triethylamine. The inorganic base includes, but not limited to, sodium hydroxide, potassium hydroxide, magnesium hydroxide, or calcium hydroxide.

Study on the stability of the aspartic acid derivative.

The aspartic acid derivative or the racemate, stereoisomer, geometric isomer, tautomer, solvate or feed-acceptable salt thereof provided in the present invention was tested at 60° C. for the stability of the compound. The test period was 10 days, during which the content of the compound did not change significantly over time.

The Present Invention Relates to Use of the Aspartic Acid Derivative.

The aspartic acid derivative and the racemate, stereoisomer, geometric isomer, tautomer, solvate or feed-acceptable salt thereof provided in the present invention is applied in preparing animal feed additives.

The term "animals" refers to human or farmed animals that cannot synthesize inorganic substances into organic substances, and can only use organic substances as food for life activities such as feeding, digestion, absorption, breathing, circulation, excretion, sensation, movement, and reproduction. "Farmed animals" include poultry, livestock, aquaculture animals, and other animals that are bred in captivity or legally captured, including pets, such as cats and dogs. The term "domestic animal" is, for example, any of pig, cattle, horse, goat, sheep, deer, and many other useful rodents. The term "poultry" includes, for example, chicken, duck, goose, quail, pigeon and the like. The term "aquaculture animal" includes, for example, fish, shrimp, tortoise, turtle and the like.

The term "feed additive" refers to a small or trace amount of substance added in the process of feed processing, production, and use, and may be a nutritional feed additive or an general feed additive, which is also called non-nutritional feed additive. The nutritional feed additive refers to a small or trace amount of substance added to compound feeds to balance feed nutrients, improve feed utilization, and directly exert nutritional effects on animals, including vitamins, trace elements, amino acids, small peptides and non-protein nitrogen. The general feed additive, also called a non-nutritional additive, refers to some non-nutritional substances that are added to feeds to improve feed utilization, ensure feed quality, and are beneficial to animal health or metabolism, including growth promoters, deworming agents, feed conditioning agents, feed conditioners, feed preservatives and Chinese herbal medicine additives.

The aspartic acid derivative or the racemate, stereoisomer, geometric isomer, tautomer, solvate or feed-acceptable salt thereof provided in the present invention is applied in preparing a non-nutritional additive for improving production performance for animals at various growth stages, where the animals can be selected from livestock, poultry, aquaculture animals or pets at various growth stages.

Further, the livestock include, but not limited to, pigs, cattle, sheep, horses, rabbits, minks or donkeys, the poultry include, but not limited to, chickens, turkeys, ducks, geese, quails or pigeons, and the aquaculture animals include, but not limited to, fish, shrimps, tortoises, crabs, turtles, bullfrogs, eel or loach, and the pets include, but not limited to, dogs or cats of various subspecies.

In an embodiment, the aspartic acid derivative or the racemate, stereoisomer, geometric isomer, tautomer, solvate or feed-acceptable salt thereof provided in the present invention is applied in preparing a feed additive for weaned pigs, which can effectively increase the average daily gain of weaned pigs and improve the feed conversion rate without affecting the feed intake.

In another embodiment, the aspartic acid derivative or the racemate, stereoisomer, geometric isomer, tautomer, solvate or feed-acceptable salt thereof provided in the present invention is applied in preparing a feed additive for laying hens, which can effectively improve the laying rate of laying hens, increase egg weight and reduce the feed-to-egg ratio of laying hens.

In another embodiment, a feed additive prepared using the aspartic acid derivative or the racemate, stereoisomer, geometric isomer, tautomer, solvate or feed-acceptable salt thereof provided in the present invention can significantly improve production performance of broilers.

In still another embodiment, the aspartic acid derivative or the racemate, stereoisomer, geometric isomer, tautomer, solvate or feed-acceptable salt thereof provided in the present invention is applied in preparing a feed additive for improving production performance of fishes.

In an embodiment, the aspartic acid derivative is a zinc salt, which is used to prepare a feed additive for animals and can be used as a substitute for high level of inorganic zinc for animals.

In another embodiment, the aspartic acid derivative is a copper salt, which is used to prepare a feed additive for animals and can be used as a substitute for high level of inorganic copper for animals.

Feed Composition Involved in the Present Invention.

A feed composition, containing at least one of the aspartic acid derivative or the racemate, stereoisomer, geometric isomer, tautomer, solvate or feed-acceptable salt thereof, and an auxiliary material usable for feed, where the auxiliary material usable for feed is a carrier, a diluent, an adjuvant, or a solvent suitable for use in feeding, or a combination thereof.

The feed involved in the present invention refers to a product that is industrially processed and manufactured for animal consumption.

The term "composition" refers to a compound set containing one or more compounds as effective ingredients.

The "comprise," "include," "contain" and variants thereof in the present invention mean an open expression, which includes the contents explicitly stated in the present invention and does not exclude contents of other aspects.

The term "carrier" refers to a substance suitable for use in feeding, which can carry active ingredients to improve their dispersity and has good chemical stability and adsorption. Carriers may be organic carriers or inorganic carriers. The organic carriers are materials containing a lot of crude fiber, including but not limited to corn flour, corn cob flour, wheat bran, rice husk flour, defatted rice bran, rice bran and hull, corn stalk flour, peanut hull flour and the like. The inorganic carriers are minerals, mainly divided into calcium salts and silicon oxides, used for the production of trace element premix, including but not limited to calcium carbonate, silicate, vermiculite, zeolite, sepiolite, etc.

The term "diluent" refers to a substance that evenly distributes the additive raw materials in the material, dilutes the high-concentration additive raw materials into a low-concentration premix agents or premix, and can separate trace ingredients from each other and reduce reactions between active ingredients, so as to increase the stability of the active ingredients without affecting the physical and chemical properties of related substances. Diluents include organic diluents and inorganic diluents. Organic diluents include, but not limited to, corn flour, degermed corn flour, dextrose (glucose), sucrose, semolina with bran, stir-fried soybean powder, wheat middling, corn gluten meal, etc. Inorganic diluents include, but not limited to, limestone, calcium dihydrogen phosphate, shell powder, kaolin (white clay), table salt, and sodium sulfate.

The adjuvant is a wetting agent that induces the inherent viscosity of the substance, an adhesive that binds the substances together, a disintegrant that breaks the entire sheet of the substance into many fine particles, a retention aid that reduces the friction between particles or an anti-sticking agent that prevents material adhesion, including but not limited to magnesium stearate, talc, vegetable oil, magnesium lauryl sulfate, starch, starch slurry, water, inorganic salt, dextrin, powdered sugar, etc.

The term "solvent" refers to the solvent required to dissolve or disperse solids, including but not limited to water, ethanol, glycerin, and the like.

In some embodiments, the feed composition further contains an additional animal feed additive and/or animal feed raw materials.

The animal feed additive is a nutritional feed additive, a general feed additive, or a medicinal feed additive.

The nutritional feed additive refers to a small or trace amount of substance added to compound feeds to balance feed nutrients, improve feed utilization, and directly exert nutritional effects on animals, including amino acids, amino acid salts and their analogs, vitamins and vitamin-like substances, mineral elements and their complexes (chelates), microbial enzyme preparations or non-protein nitrogen.

The general feed additive, also called a non-nutritional additive, refers to some non-nutritional substances that are added to feeds to improve feed utilization, ensure feed quality, and are beneficial to animal health or metabolism, including growth promoters, deworming agents, flavorings and attractants, feed conditioning agents, feed conditioners, probiotics, prebiotics, feed preservatives and Chinese herbal medicine additives.

Further specifically, the non-nutritional additive is a growth promoter, including but not limited to butyric acid, calcium butyrate, sodium butyrate, tannic acid, p-thymol, p-thymol ester, p-thymol salt, 2-hydroxybenzoic acid, β-acid, β-acid ester, β-acid salt, hexahydro-β-acid, hexahydro-β-acid ester, hexahydro-β-acid salt, benzoic acid or calcium benzoate, zinc oxide, zinc sulfate, and zinc chloride.

In an embodiment, the non-nutritional additive is calcium butyrate.

In another embodiment, the non-nutritional additive is tannic acid.

Specifically, the medicinal feed additive includes, but not limited to, a premixed veterinary drug that has the functions of preventing animal diseases and promoting animal growth and can be added to feeds and mixed with a carriers or diluent for long-term use.

Still further specifically, the medicinal feed additive is a feed antibiotic, and the feed antibiotic includes, but not limited to, polymyxin, salinomycin, avilamycin, bacitracin, virginiamycin, nasitide, flavomycin, enramycin, kitasamycin, olaquindox, oxytetracycline, or chlortetracycline.

In some embodiments, the composition containing the aspartic acid derivative and the racemate, stereoisomer, geometric isomer, tautomer, solvate or feed-acceptable salt thereof further contains one or more of nutritional feed additive, general feed additive, and medicinal feed additive.

In some embodiments, the animal feed raw materials are substances suitable for use in feeding, such as: grains and their processed products; oilseeds and their processed products; leguminous crop seeds and their processed products; stem tubers, root tubers and their processed products; other seed and fruit products and their processed products; forage, roughage and their processed products; other plants, algae and their processed products; dairy products and their by-products; terrestrial animal products and their by-products; fish, other aquatic organisms and their by-products; minerals, microbial fermentation products and by-products; other feed raw materials.

Use of the Feed Composition.

The present invention relates to an application of the above feed composition containing the aspartic acid derivative and the racemate, stereoisomer, geometric isomer, tautomer, solvate or feed-acceptable salt thereof.

In some embodiments, The feed composition containing the aspartic acid derivative and the racemate, stereoisomer, geometric isomer, tautomer, solvate or feed-acceptable salt thereof is applied in preparing an animal feed additive.

The animal feed additive prepared using the feed composition containing the aspartic acid derivative and the racemate, stereoisomer, geometric isomer, tautomer, solvate or feed-acceptable salt thereof is a feed additive for livestock, a feed additive for poultry, a feed additive for aquaculture animals, or a feed additive for pets.

Specifically, the feed composition containing the aspartic acid derivative and the racemate, stereoisomer, geometric isomer, tautomer, solvate or feed-acceptable salt thereof is applied in preparing a feed additive for livestock, where the livestock include, but not limited to, pigs, cattle, sheep, horses, rabbits, minks, etc. at various growth stages.

Specifically, the feed composition containing the aspartic acid derivative and the racemate, stereoisomer, geometric isomer, tautomer, solvate or feed-acceptable salt thereof is applied in preparing a feed additive for poultry, where the poultry include, but not limited to, chickens, ducks, geese, pigeons etc. at various growth stages.

Specifically, the feed composition containing the aspartic acid derivative and the racemate, stereoisomer, geometric isomer, tautomer, solvate or feed-acceptable salt thereof is applied in preparing a feed additive for aquaculture animals, where the aquaculture animals include, but not limited to, fish, shrimps, crabs, turtles, eel, etc. at various growth stages.

Specifically, the feed composition containing the aspartic acid derivative and the racemate, stereoisomer, geometric isomer, tautomer, solvate or feed-acceptable salt thereof is applied in preparing a feed additive for pets, where the pets include, but not limited to, dogs or cats bred in captivity.

In some embodiments, the animal feed additive prepared using the composition containing the aspartic acid derivative and the racemate, stereoisomer, geometric isomer, tautomer, solvate or feed-acceptable salt thereof is premix, multi-premix, liquid or granule.

In some embodiments, the feed composition containing the aspartic acid derivative and the racemate, stereoisomer, geometric isomer, tautomer, solvate or feed-acceptable salt thereof is applied in preparing an animal feed.

The animal feed prepared using the feed composition containing the aspartic acid derivative and the racemate, stereoisomer, geometric isomer, tautomer, solvate or feed-acceptable salt thereof is a feed for livestock, a feed for poultry, a feed for aquaculture animals, or a feed for pets.

Specifically, the feed composition containing the aspartic acid derivative and the racemate, stereoisomer, geometric isomer, tautomer, solvate or feed-acceptable salt thereof is applied in preparing a feed for livestock, where the livestock include, but not limited to, pigs, cattle, sheep, horses, rabbits, minks, etc. at various growth stages.

Specifically, the feed composition containing the aspartic acid derivative and the racemate, stereoisomer, geometric isomer, tautomer, solvate or feed-acceptable salt thereof is applied in preparing a feed for poultry, where the poultry include, but not limited to, chickens, ducks, geese, pigeons etc. at various growth stages.

Specifically, the feed composition containing the aspartic acid derivative and the racemate, stereoisomer, geometric isomer, tautomer, solvate or feed-acceptable salt thereof is applied in preparing a feed for aquaculture animals, where the aquaculture animals include, but not limited to, fish, shrimps, crabs, turtles, eel, etc. at various growth stages.

Specifically, the feed composition containing the aspartic acid derivative and the racemate, stereoisomer, geometric isomer, tautomer, solvate or feed-acceptable salt thereof is applied in preparing a feed for pets, where the pets include, but not limited to, dogs or cats bred in captivity.

In some embodiments, the feed prepared using the feed composition containing the aspartic acid derivative and the racemate, stereoisomer, geometric isomer, tautomer, solvate or feed-acceptable salt thereof is a single feed, concentrated feed, formula feed, multi-premix or concentrate supplement.

Specifically, the compound feed is a complete formula feed.

Method for Improving Production Performance of Farmed Animals.

In some feeding embodiments, farmers feed the feed additive or feed containing the aspartic acid derivative and the racemate, stereoisomer, geometric isomer, tautomer, solvate or feed-acceptable salt thereof to animals together with a feed, which can effectively improve production performance of farmed animals.

In some embodiments, the feed additive or feed is premix, multi-premix, granule or liquid, which is fed to animals after being mixed with an animal feed.

The animals are livestock, poultry, aquaculture animals, or pets.

Specifically, the livestock include, but not limited to, pigs, cattle, sheep, horses, rabbits, minks, etc. at various growth stages; the poultry include, but not limited to, chickens, ducks, geese, pigeons etc. at various growth stages; the aquaculture animals include, but not limited to, fish, shrimps, crabs, turtles, eel, etc. at various growth stages; and the pets include, but not limited to, dogs or cats bred in captivity.

In some embodiments, farmers feed the feed additive or feed containing the aspartic acid derivative and the racemate, stereoisomer, geometric isomer, tautomer, solvate or feed-acceptable salt thereof to weaned pigs together with a feed, which can significantly increase the feed intake and the average daily gain of weaned pigs and effectively improve the feed conversion rate.

In a specific embodiment, the aspartic acid derivative contained in the feed additive or feed that farmers feed to weaned pigs together with the feed is a zinc salt of N-carbamoyl aspartic acid, which significantly increases the feed intake and the average daily gain of weaned pigs and effectively improves the feed conversion rate, and the feed additive reaches the level of improvement on the production performance of weaned pigs that can be achieved by high level of inorganic zinc.

In another specific embodiment, the aspartic acid derivative contained in the feed additive or feed that farmers feed to weaned pigs together with the feed is a copper salt of N-carbamoyl aspartic acid, which significantly increases the average daily gain of weaned pigs and effectively improves the feed conversion rate, and the feed additive reaches the level of improvement on the production performance of weaned pigs that can be achieved by high level of inorganic copper.

In an embodiment, farmers feed the feed additive or feed containing the aspartic acid derivative and the racemate, stereoisomer, geometric isomer, tautomer, solvate or feed-acceptable salt thereof to broilers together with a feed, which can effectively increase the weight gain and significantly reduce the feed conversion ratio of broilers, thereby improving the feed conversion rate.

In an embodiment, farmers feed the feed additive or feed containing the aspartic acid derivative and the racemate, stereoisomer, geometric isomer, tautomer, solvate or feed-acceptable salt thereof to laying hens together with a feed, which significantly improves the laying rate, increases egg weight and reduces the feed-to-egg ratio.

In an embodiment, farmers feed the feed additive or feed containing the aspartic acid derivative and the racemate, stereoisomer, geometric isomer, tautomer, solvate or feed-acceptable salt thereof to fish together with a feed.

In an embodiment, farmers feed the feed additive or feed containing the aspartic acid derivative and the racemate, stereoisomer, geometric isomer, tautomer, solvate or feed-acceptable salt thereof to puppies together with a feed.

In some other feeding embodiments, farmers feed the feed composition containing the aspartic acid derivative and the racemate, stereoisomer, geometric isomer, tautomer, solvate or feed-acceptable salt thereof to animals, which can significantly improve the production performance of animals.

Optionally, the feed composition is feed additive premix, feed additive multi-premix, granule or liquid, which is fed to animals together with a feed.

In an embodiment, the feed composition is feed additive premix.

In an embodiment, the feed composition is feed additive multi-premix.

Optionally, the feed composition is a concentrated feed, formula feed, multi-premix or concentrate supplement, which is directly fed to animals as an animal feed.

In an embodiment, the feed composition is a complete formula feed.

Now some embodiments of the present invention will be described in detail, examples of which will be illustrated by the accompanying structural formulas and chemical formulas. The present invention is intended to cover all alternatives, modifications and equivalent technical solutions, which are all included in the scope of the present invention as defined by the claims. In addition, for purpose of clarity, some technical features of the present invention are described separately in multiple independent embodiments, but they can also be provided in combination or provided in any suitable sub-combination in a single embodiment.

DETAILED DESCRIPTION OF THE EMBODIMENTS

To make the objects, the technical solution, and advantages of the present invention clearer, the compounds, the combinations, and the use of the present invention are described in further detail with reference to examples. It should be understood that the specific embodiments described herein are merely used for explaining the present invention, and are not intended to limit the present invention.

Example 1: Preparation of Compounds

Example 1.1 Preparation of N-carbamoyl-DL-aspartic acid

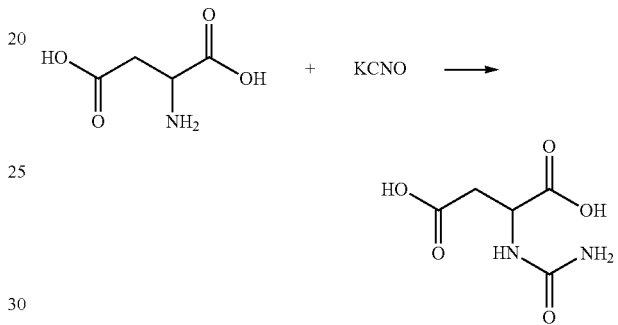

13 g of DL-aspartic acid and 8 g of potassium cyanate were dissolved in 100 mL of 1 mol/L potassium hydroxide solution at room temperature with stirring at room temperature for 16 h, and the reaction mixture was adjusted to pH 2 with concentrated hydrochloric acid, and then stirred for 1.0 h to precipitate a solid, which was filtered and slurried with water to give 10.5 g of white solid. The yield was 68%. 1H NMR (500 MHz, DMSO-$d_6$) δ: 12.48 (s, 2H), 6.28 (d, 1H), 5.72 (s, 2H), 4.35-4.38 (m, 1H), 2.56-2.67 (m, 2H).

Example 2 Preparation of N-glycyl-DL-aspartic acid

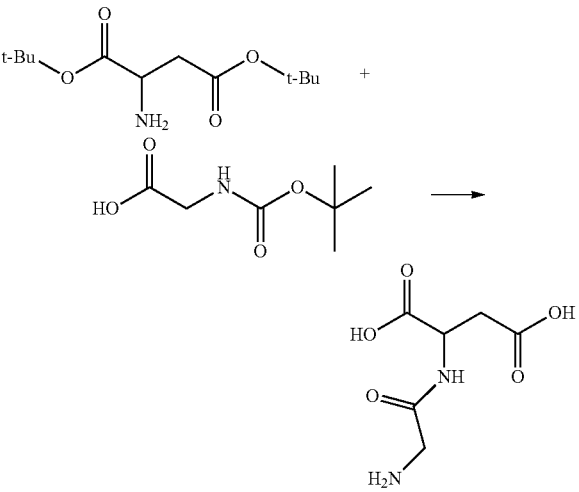

1.1 g of N-Boc-glycine, 1.6 g of di-tert-butyl DL-aspartate and 2.6 g of HBTU were dissolved in 15 mL of dry DMF, and diisopropylethyl amine was added under the protection of nitrogen and the resulting reaction mixture was reacted overnight at room temperature. After the reaction, 100 mL of ethyl acetate was added to the reaction mixture, and the resulting organic phase was washed sequentially with 30 mL of 1N sodium bicarbonate solution and 30 mL of 1N hydrochloric acid aqueous solution, and then dried over magnesium sulfate. The organic solvent was removed by rotary evaporation and the crude product obtained was purified by a silica gel column chromatography (dichloromethane/methanol (v:v)=96:5) to give 1.5 g of di-tert-butyl N—(N-Boc-glycyl)-aspartate. The yield was 60%.

The di-tert-butyl N—(N-Boc-glycyl)-aspartate obtained in the above step was dissolved in 100 mL of dry dichloromethane, 8 mL of trifluoroacetic acid was added, stirred at room temperature and reacted for 24 h, and then washed with water (50 mL×3), followed by reduced pressure and concentration to remove the solvent. The obtained crude product was recrystallized in ethyl acetate to obtain 0.6 g of N-glycyl-DL-aspartic acid, with a yield of 72.7%.

Example 2: Test for Studying the Thermal Stability of Compounds

The variations of the contents of the main ingredient of the aspartic acid derivative raw material and the main ingredient of a premix containing 2% mass fraction of the aspartic acid derivative (hereinafter referred to as 2% premix) over time were investigated under the conditions of stability test at 60° C.

Experimental apparatus: drug stability incubator, Waters high-performance liquid chromatograph (HPLC), etc.

Test samples: N-carbamoyl-DL-aspartic acid (compound 1), diethyl N-carbamoyl-DL-aspartate (compound 2), Sodium N-carbamoyl-DL-aspartate (compound 3), Calcium N-carbamoyl-DL-aspartate (compound 4), Zinc N-carbamoyl-DL-aspartate (compound 5), Copper N-carbamoyl-DL-aspartate (compound 6), Iron N-carbamoyl-DL-aspartate (compound 7), N-glycyl-DL-aspartic acid (compound 8), N-(4-aminobutyryl)-DL-aspartic acid (compound 9), N-(10-aminodecanoyl)-DL-aspartic acid (compound 10), N-(14-aminomyristoyl)-DL-aspartic acid (compound 11).

Experimental reagents: methanol (chromatographic grade), phosphoric acid (analytically pure).

Experimental Steps:

Preparation of standard solution: 50 mg of the test sample raw material was ultrasonically dissolved in 50 mL of water to obtain a working reserve solution. An appropriate amount of the working reserve solution was taken and diluted with water respectively to concentrations of 125 ppm, 250 ppm, 500 ppm, and 1000 ppm for HPLC testing. It was checked whether the sample concentrations are in a linear relationship with the peak area response values in HPLC, and a standard curve was established.

Preparation of test solution: An appropriate amount of the test sample raw material and an appropriate amount of a premix containing 2% mass fraction of the test sample (hereinafter referred to as 2% premix) were separately ultrasonically dissolved in an appropriate amount of water to form a 1000 ppm solution, which is filtered through a 0.22 μm filter membrane and then analyzed by HPLC.

HPLC analysis conditions: chromatographic column: Waters C18 column (250 mm×4.6 mm, 5 μm); mobile phase: 0.05% phosphoric acid:methanol=95:5 (v:v) (raw material); 0.05% phosphoric acid:methanol (gradient elution); methanol: 5%→40% (0-15 min) curve 6, 40%→5% (15-16 min) curve 1, 5% (16-23 min) curve 1, (premix, feed); detection wavelength: 210 nm; column temperature: 25° C.; sample size: 20 μL; flow rate: 1 mL/min.

Test method: The test sample raw material and its 2% premix were placed in a culture plate, spread into a thin layer of ≤5 mm, and placed at 60° C. Samples were taken on the day 5 and 打 day 10 for HPLC detection. Each sample was sampled three times in parallel.

Test results: The test results are expressed as "mean values", as shown in Table 1. The test results show that in the test period of 0-10 days, except that the content of the Iron N-carbamoyl-DL-aspartate dropped to 94.98% on the 10th day, the contents of the raw material of each test sample and its 2% premix did not change significantly under high temperature conditions at 60° C., exhibiting excellent stability.

TABLE 1

Study on the thermal stability of compounds

| Test sample | Dosage form | Detection result of the content of test sample (%) | |
| --- | --- | --- | --- |
| | | Day 5 | Day 10 |
| Compound 1 | Raw material | 99.79 | 99.28 |
| | 2% premix | 99.66 | 99.70 |
| Compound 2 | Raw material | 97.32 | 96.97 |
| | 2% premix | 98.81 | 98.09 |
| Compound 3 | Raw material | 103.02 | 103.53 |
| | 2% premix | 99.33 | 99.21 |
| Compound 4 | Raw material | 101.54 | 101.87 |
| | 2% premix | 98.93 | 97.99 |
| Compound 5 | Raw material | 99.76 | 98.47 |
| | 2% premix | 96.89 | 96.36 |
| Compound 6 | Raw material | 99.91 | 98.31 |
| | 2% premix | 98.28 | 97.94 |
| Compound 7 | Raw material | 97.63 | 96.01 |
| | 2% premix | 96.74 | 94.98 |
| Compound 8 | Raw material | 99.78 | 98.02 |
| | 2% premix | 98.57 | 97.32 |
| Compound 9 | Raw material | 98.46 | 98.09 |
| | 2% premix | 99.41 | 97.68 |
| Compound 10 | Raw material | 99.00 | 96.73 |
| | 2% premix | 98.55 | 97.81 |
| Compound 11 | Raw material | 97.61 | 95.93 |
| | 2% premix | 98.22 | 97.80 |

Note:
Characterization method for detection result of the content of test sample: The detection result of the content of the test sample is obtained by comparing the result of measurement performed by an instrument on the test sample sample at a specific time in each test with the measurement result obtained on Day 0, where if the detection result of the content changes by 5% or more, it is determined that a significant change occurs.

Example 3: Breeding Test

Example 3.1 the Effect of the Aspartic Acid Derivative and Salt Thereof on the Production Performance of Weaned Piglets From 95 litters of 28±2 days old Duroc×Landrace×Yorkshire cross-bred weaned piglets, 360 clinically healthy piglets with similar body weights were selected as test pigs, which were randomly divided into 12 groups, with 3 replications per group and 10 pigs (half of male and female) per replication. The piglets were attracted to the food trough at the age of 7 days, and the hog house for 28-day-old weaned pigs has a cement floor, steel fence, good ventilation, and suitable temperature. The pigpens and utensils were sterilized before the test. During the test period, the test pigs were free-stall housed in the same pigpen under the same feeding and management conditions, and were free to drink water and eat feed. The hog house was cleaned once a day, and the floor is washed once every three days to maintain clean and hygienic conditions. The test pigs were fed three times a day. The test groups include control and test groups. Group I is the control group, in which only the basal daily ration was fed to the piglets. 50 ppm of the aspartic acid derivative was added into the basal daily ration for the piglets in the test groups II-VII, as shown in Table 2. 1000 ppm of a the aspartic acid derivative metal ion salt was added into the basal daily ration for the piglets in the groups VIII-XII, as shown in Table 2. No other antioxidant ingredients or growth promoters were added for the test groups during the entire feeding process. The test period was 40 days.

The test pigs were weighed during 7:00 to 9:00 in the morning of Day 0 and Day 40 after the start of the test. During the test period, the feed intake and health status of the piglets were observed every day, the remaining daily ration was weighed, the feed consumption was recorded, and the average daily feed intake (ADFI, g/d*each pig), the average daily gain (ADG, g/d*each pig), and the feed conversion ratio (FCR) were calculated. Calculation formulas are as follows:

Average daily feed intake=(total amount of feed−
remaining amount of feed)/(number of days of
test×number of pigs per repetition);

Average daily gain=(average body weight at the end
of the test−average body weight at the beginning of the test)/number of days of test;

Feed conversion ratio=average daily feed intake/
average daily gain.

The test data was statistically analyzed using SPSS18 software. First, a one-way analysis of variance (ANOVA) was performed on the data. If the difference between treatments is significant, Duncan's method was used for multiple comparisons, and the significance level was 0.05. The test results are expressed as "mean value±standard deviation", and are as shown in Table 2.

It can be seen from the results of the feeding tests for weaned piglets that by comparison between the test groups and the control group, all the test samples except diethyl N-carbamoyl-DL-aspartate, Sodium N-carbamoyl-DL-aspartate and Zinc N-carbamoyl-DL-aspartate have no obvious impact on the feed intake of weaned pigs. In terms of average daily gain, N-carbamoyl-DL-aspartic acid, N-glycyl-DL-aspartic acid, and N-(4-aminobutyryl)-DL-aspartic acid increased the average daily gain of the test pigs by 7.0%, 5.2%, 8.1% respectively, which, however, are not significant compared with that of the control group. The other test groups had a significant effect in increasing the average daily gain of the test pigs compared with the control group. In terms of feed conversion rate, the feed conversion rates of each test group decreased by 4.8%-7.8%, and there was no significant improvement effect compared with the control group.

TABLE 2

Study on the effect of aspartic acid derivatives and their salts on the production performance of weaned piglets

| | Test sample/content: (ppm) | ADFI (g/d * each pig) | ADG (g/d * each pig) | FCR |
|---|---|---|---|---|
| Group I | — | 310 ± 18$^a$ | 135 ± 4$^a$ | 2.29 ± 0.07 |
| Group II | N-carbamoyl-DL-aspartic acid 45 | 315 ± 14$^a$ | 145 ± 10$^{abc}$ | 2.18 ± 0.05 |
| Group III | N-glycyl-DL-aspartic acid 45 | 305 ± 12$^a$ | 142 ± 1$^{ab}$ | 2.15 ± 0.07 |
| Group IV | N-(4-aminobutyryl)-DL-aspartic acid 45 | 311 ± 18$^a$ | 146 ± 4$^{abc}$ | 2.13 ± 0.06 |
| Group V | N-(10-aminodecanoyl)-DL-aspartic acid 45 | 321 ± 7$^a$ | 150 ± 1$^{bc}$ | 2.14 ± 0.06 |
| Group VI | N-(14-aminomyristoyl)-DL-aspartic acid 45 | 322 ± 16$^a$ | 150 ± 4$^{bc}$ | 2.14 ± 0.05 |
| Group VII | diethyl N-carbamoyl-DL-aspartate 45 | 374 ± 11$^b$ | 176 ± 2$^d$ | 2.13 ± 0.05 |
| Group VIII | Sodium N-carbamoyl-DL-aspartate 1000 | 388 ± 11$^{bc}$ | 182 ± 2$^d$ | 2.13 ± 0.04 |
| Group IX | Calcium N-carbamoyl-DL-aspartate 1000 | 333 ± 8$^a$ | 157 ± 0$^c$ | 2.13 ± 0.05 |
| Group X | Zinc N-carbamoyl-DL-aspartate 1000 | 418 ± 19$^c$ | 198 ± 3$^6$ | 2.11 ± 0.07 |
| Group XI | Copper N-carbamoyl-DL-aspartate 1000 | 329 ± 13$^a$ | 156 ± 1$^c$ | 2.11 ± 0.07 |
| Group XII | Iron N-carbamoyl-DL-aspartate 1000 | 330 ± 11$^a$ | 153 ± 1$^{bc}$ | 2.15 ± 0.06 |

Note:
Data in the same column labeled with different letters indicates a significant difference (P < 0.05)

Example 3.2 the Effect of the Aspartic Acid Derivative and Salt Thereof on the Production Performance of Laying Hens The test adopted a single-factor random design. 420 147-day-old Jingbai laying hens with similar body weights were selected and randomly divided into 7 treatment groups, with 3 replications per group and 20 Jingbai laying hens (half of male and female) per replication. The poultry houses and utensils were sterilized before the test. During the test period, the Jingbai laying hens were cage cultured in the same laying poultry house under the same feeding and management conditions. The basal daily ration was mainly corn-soybean meal, and no other antioxidant ingredients or growth promoters were added additionally during the entire feeding process. The test groups include a control group and test groups I-VII. The basal daily ration was fed for the control group I only, and 500 ppm of different aspartic acid derivatives were added into the basal daily ration for the test groups II-VII, as shown in Table 3. The pre-feeding period was 10 days, and the test period was 158 days. The test laying hens were free to drink water and eat feed, and were fed twice a day.

Parameter statistics: During the test period, taking each repetition as a unit, the total egg number, the egg production, and the feed intake were recorded every day, and the egg production rate (EPR), the average daily feed intake (ADFI, g/d), the egg weight (EW, g) and the feed-to-egg ratio (FER) of the laying hens during the entire test were calculated.

Calculation formulas are as follows:

Egg production rate (%)=average daily total egg
number/number of laying hens×100;

Egg weight (g)=average daily total egg weight/average daily total egg number;

Feed-to-egg ratio=average daily feed intake/egg weight.

The test data was statistically analyzed using SPSS18 software. First, a one-way analysis of variance (ANOVA) was performed on the data. If the difference between treatments is significant, Duncan's method was used for multiple comparisons, and the significance level was 0.05. The test results are expressed as "mean value±standard deviation", and are as shown in Table 4.

It can be seen from the results that the effects of the test samples on the egg production rate and feed-to-egg ratio of the test laying hens were not significant compared with the control group, but reflected different degrees of improvement, where the egg production rate was increased by 2.7%-4.4% and the feed-to-egg ratio was decreased by 5.9%-7.6%; the test samples had no effect on the feed intake of the test laying hens, but the egg weights of all the groups except N-glycyl-DL-aspartic acid were increased significantly.

TABLE 3

Test groups of use of aspartic acid derivatives in feeds for laying hens

| | Test sample | Content (ppm) |
|---|---|---|
| Group I | — | — |
| Group II | N-carbamoyl-DL-aspartic acid | 500 |
| Group III | N-glycyl-DL-aspartic acid | 500 |
| Group IV | N-(4-aminobutyryl)-DL-aspartic acid | 500 |
| Group V | N-(10-aminodecanoyl)-DL-aspartic acid | 500 |
| Group VI | N-(14-aminomyristoyl)-DL-aspartic acid | 500 |
| Group VII | diethyl N-carbamoyl-DL-aspartate | 500 |

TABLE 4

Study on the effect of use of aspartic acid derivatives in feeds for laying hens

| | EPR (%) | ADFI (g/d) | EW (g) | EPR |
|---|---|---|---|---|
| Group I | $82.61 \pm 0.17^a$ | $119.56 \pm 1.21$ | $54.23 \pm 0.38^a$ | $2.21 \pm 0.02^a$ |
| Group II | $85.80 \pm 0.14^b$ | $113.44 \pm 1.55$ | $55.49 \pm 0.38^b$ | $2.04 \pm 0.02^b$ |
| Group III | $84.86 \pm 0.24^c$ | $113.01 \pm 2.31$ | $54.98 \pm 0.39^a$ | $2.06 \pm 0.03^b$ |
| Group IV | $86.09 \pm 0.18^b$ | $113.64 \pm 2.43$ | $55.44 \pm 0.37^b$ | $2.05 \pm 0.04^b$ |
| Group V | $85.24 \pm 0.18^c$ | $119.31 \pm 1.84$ | $57.45 \pm 0.47^c$ | $2.08 \pm 0.03^b$ |
| Group VI | $85.24 \pm 0.17^c$ | $115.13 \pm 2.91$ | $55.45 \pm 0.35^b$ | $2.08 \pm 0.04^b$ |
| Group VII | $86.28 \pm 0.20^b$ | $115.19 \pm 3.14$ | $55.94 \pm 0.37^b$ | $2.06 \pm 0.04^b$ |

Note:
Data in the same column labeled with different letters indicates a significant difference (P <0.05)

Example 3.3 the Effect of the Aspartic Acid Derivative and Salt Thereof on the Production Performance of Broilers The test adopted a single-factor random design. 420 1-day-old yellow-feathered broilers with similar body weights and having an average weight of 50 g were selected and randomly divided into 7 treatment groups, with 3 replications per group and 20 yellow-feathered broilers (half of male and female) per replication. The poultry houses and utensils were sterilized before the test. During the test period, the Jingbai laying hens were cage cultured in the same laying henhouse under the same feeding and management conditions. The basal daily ration was mainly corn-soybean meal, and no other antioxidant ingredients or growth promoters were added additionally during the entire feeding process. The test groups include a control group and test groups I-VII. The basal daily ration was fed for the control group I only, and 300 ppm of different aspartic acid derivatives were added into the basal daily ration for the test groups II-VII, as shown in Table 5. The test period was 20 days. The test yellow-feathered broilers were free to drink water and cat feed, and were fed twice a day. Taking each repetition as a unit, the test broilers were weighed at the age of 21 days (where provisioning of feeds was stopped for 12 hours, but provisioning of water was not stopped), the feed consumption of the test broilers were calculated, and the average daily feed intake (ADFI, g/d*each broiler), the average daily gain (ADG, g/d*each broiler) and the feed conversion ratio (FCR) were calculated for the test broilers of each group. Calculation formulas are as follows:

Feed conversion ratio (FCR)=average daily feed intake/average daily gain.

The test data was statistically analyzed using SPSS18 software. First, a one-way analysis of variance (ANOVA) was performed on the data. If the difference between treatments is significant, Duncan's method was used for multiple comparisons, and the significance level was 0.05. The test results are expressed as "mean value±standard deviation", and are as shown in Table 5.

It can be seen from the results that the effects of the aspartic acid derivative test samples in the test groups on the feed intake have different degrees of improvement compared with the control group; compared with the control group, the average daily gains of the test broilers in the test groups were all increased, wherein the effects of N-carbamoyl-DL-aspartic acid and diethyl N-carbamoyl-DL-aspartate were the most significant; in terms of feed conversion ratio, compared with the control group, the feed conversion ratios of the test groups were decreased by about 3.1% to 7.0%, and significant improvement effects were observed in some test groups. On the whole, the aspartic acid derivatives used in the tests have excellent effects on the improvement of production performance of broilers both in terms of average daily gain and feed conversion ratio.

TABLE 5

Study on the effect of use of aspartic acid derivatives in feeds for broilers

| | Test sample/content: (ppm) | ADFI (g/d * each broiler) | ADG (g/d * each broiler) | FCR |
|---|---|---|---|---|
| Group I | — | $34.63 \pm 0.71^a$ | $13.48 \pm 0.14^a$ | $2.57 \pm 0.03^a$ |
| Group II | N-carbamoyl-DL-aspartic acid 300 | $38.83 \pm 0.53$ | $16.59 \pm 0.14^b$ | $2.34 \pm 0.03^b$ |

TABLE 5-continued

Study on the effect of use of aspartic acid derivatives in feeds for broilers

| | Test sample/content: (ppm) | ADFI (g/d * each broiler) | ADG (g/d * each broiler) | FCR |
|---|---|---|---|---|
| Group III | N-glycyl-DL-aspartic acid 300 | 36.05 ± 0.83$^b$ | 14.48 ± 0.24$^b$ | 2.49 ± 0.03$^{ab}$ |
| Group IV | N-(4-aminobutyryl)-DL-aspartic acid 300 | 37.92 ± 0.53$^c$ | 15.84 ± 0.10$^b$ | 2.39 ± 0.04$^b$ |
| Group V | N-(10-aminodecanoyl)-DL-aspartic acid 300 | 34.82 ± 0.64$^a$ | 14.40 ± 0.15$^b$ | 2.42 ± 0.04$^b$ |
| Group VI | N-(14-aminomyristoyl)-DL-aspartic acid 300 | 36.70 ± 0.54$^{ac}$ | 15.02 ± 0.13$^b$ | 2.44 ± 0.04$^b$ |
| Group VII | diethyl N-carbamoyl-DL-aspartate 300 | 40.05 ± 0.81$^d$ | 16.81 ± 0.68$^b$ | 2.39 ± 0.05$^b$ |

Note:
Data in the same column labeled with different letters indicates a significant difference (P <0.05).

Table 3.4 Use of aspartic acid derivatives in feeds for fish
1) Test Materials

Test fish: The test fishes used were healthy and lively grass carp fingerlings with uniform size, which were fed in large cages for 4 weeks before being used for formal breeding test. The experimental system was a small floating cage (specification: 1.1×1.1×1.1 m$^3$), each small floating cage being equipped with an aeration head, providing aeration 24 h a day. Both the small floating cage and the temporary cage were placed in a 3500 m$^2$ pond of the test field, the depth of the pond was about 1.5 m, and the water of the pond was fully aerated in the bottom of the pond. 560 grass carps that were hungry for 1 day were randomly divided into 7 groups, with 4 replications per group and 20 grass carps per replication. By taking each replication as a unit, all of the grass carps were weighed, and then placed in 28 cages and fed with test feeds containing different test samples at the same content level.

Test feeds: The feeds for the test were self-prepared based on the formulations in Table 6, and different test samples were added at the same content level for different test groups according to Table 7, respectively.

The feed raw materials used were ground by ultrafine grinding and fed into a puffing machine produced by Jiangsu Muyang Group Co., Ltd. to make 3 mm floating puffed feed, where the mold clearing temperature was 130° C., 3% soybean oil was sprayed using an oil spraying equipment, and the obtained feed was sealed and stored in a cool place for later use.

TABLE 6

Formulations and chemical compositions of test feeds for grass carps (wt. %)

| Raw material composition | Content (%) |
|---|---|
| Fish meal | 9.0 |
| Casing powder | 3.0 |
| Soybean meal | 12.0 |
| Rapeseed meal | 12.0 |
| Monosodium glutamate protein | 3.0 |
| Brown shorts | 12.6 |
| Flour | 17.0 |
| Bentonite | 0.70 |
| Rice bran | 10.0 |
| Soybean oil | 3.0 |
| Phospholipid rapeseed meal | 9.0 |
| Wheat gluten powder | 4.0 |
| Blood cell powder | 2.0 |
| Vc-phosphate | 0.1 |
| Calcium dihydrogen phosphate | 1.8 |
| Choline chloride | 0.2 |
| Multi-vitamin premix | 0.1 |
| Trace-mineral premix | 0.5 |

TABLE 7

Test groups for the study of use of aspartic acid derivatives in feeds for fish

| Group | Test sample | Dose (ppm) |
|---|---|---|
| Group I | — | — |
| Group II | N-carbamoyl-DL-aspartic acid | 3000 |
| Group III | N-glycyl-DL-aspartic acid | 3000 |
| Group IV | N-(4-aminobutyryl)-DL-aspartic acid | 3000 |
| Group V | N-(10-aminodecanoyl)-DL-aspartic acid | 3000 |
| Group VI | N-(14-aminomyristoyl)-DL-aspartic acid | 3000 |
| Group VII | diethyl N-carbamoyl-DL-aspartate | 3000 |

(2) Test Method

Test management: The test adopted controlled artificial feeding, and the feeding amount was adjusted once a week. The feeding levels for all the groups (based on the initial fish weight) were exactly the same, and the grass carps were fed twice a day (7:30 and 15:00). The total feeding amount was 580 g/replication test group. The test period was 8 weeks. During the test, the water quality was regularly monitored. The water temperature during the whole breeding process was 26.88±3.08° C., DO>5.0 mg O L$^{-1}$, pH 7.8, ammonia nitrogen<0.50 mg N L$^{-1}$, nitrite nitrogen<0.05 mg N L$^{-1}$.

Parameter statistics: During the test, after the provisioning of feeds has been stopped for 1 day, fishes in each cage were weighed as a whole, and the weight gain (WG, %) and the feed conversion ratio (FCR) were calculated. Calculation formulas are as follows:

Weight gain (WG,%)=100×(average final weight–average initial weight)/average initial weight;

Feed conversion ratio (FCR)=feed intake/weight gain of fish body.

(3) Test Results

It can be seen from the test results shown in Table 8 that the use of the aspartic acid derivatives in feeds for aquatic products had an effect of improving the production performance of grass carps, which was reflected by the increases in the weight gain and the improvement in the feed conversion ratio. The weight gain of each test group was improved, wherein the weight gains of the test groups fed with N-glycyl-DL-aspartic acid and diethyl N-carbamoyl-DL-aspartate had a significant improvement effect compared with the control group. Compared with the control group, the feed conversion ratios of the test groups were all significantly declined, which improved the utilization of feeds.

TABLE 8

Test results of use of aspartic acid derivatives in feeds for aquatic products

| | Average initial weight (g) | Average final weight (g) | Weight gain (%) | (FCR) |
|---|---|---|---|---|
| Group I | 425.2 ± 4.8 | 757.0 ± 3.5$^a$ | 78.02 ± 1.20$^a$ | 1.749 ± 0.008$^a$ |
| Group II | 423.0 ± 5.5 | 774.5 ± 4.8$^b$ | 83.19 ± 1.41$^b$ | 1.650 ± 0.011$^b$ |
| Group III | 431.0 ± 5.9 | 778.2 ± 4.3$^b$ | 80.62 ± 1.46 | 1.671 ± 0.008$^b$ |
| Group IV | 432.5 ± 6.1 | 781.8 ± 4.4$^b$ | 80.76 ± 1.52 | 1.662 ± 0.008$^b$ |
| Group V | 430.2 ± 4.6 | 781.0 ± 5.1$^b$ | 81.58 ± 0.96 | 1.653 ± 0.009$^b$ |
| Group VI | 422.0 ± 5.0 | 769.2 ± 4.5$^{ab}$ | 82.32 ± 1.24 | 1.671 ± 0.008$^b$ |
| Group VII | 420.2 ± 6.8 | 772.0 ± 6.3$^b$ | 83.74 ± 1.53$^b$ | 1.650 ± 0.008$^b$ |

Note:
Data in the same column labeled with different letters indicates a significant difference (P <0.05).

The above-mentioned embodiments only describe several implementations of the present invention, and there are other ways to implement the present invention. Correspondingly, the embodiments of the present invention are described as examples, but they should not be interpreted as limiting the patent scope of the present invention, and the present invention also encompasses modifications made within the scope of the present invention and based on the same inventive concept or equivalent contents added in the claims.

What is claimed is:

1. A feed composition comprising an aspartic acid derivative having a structure represented by the following general formula, or a racemate, stereoisomer, geometric isomer, tautomer, or solvate thereof, and an auxiliary material usable for feed,

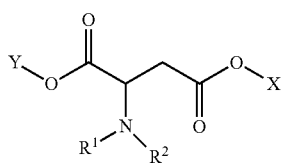

wherein $R^1$ is $R^{1a}C(=O)-$ or $-H$; $R^2$ is $R^{2a}C(=O)-$; the $R^{1a}$ and $R^{2a}$ are independently selected from $(A)(B)N-(CH_2)_{0-5}-$, and the A and B are independently selected from a $C_1$-$C_{20}$ alkyl or $-H$; and Y and X are independently selected from a $C_1$-$C_{20}$ alkyl or $-H$.

2. The feed composition according to claim 1, wherein the feed composition further comprises an additional animal feed additive, and the additional animal feed additive is selected from a nutritional feed additive, a non-nutritional feed additive or a medicinal feed additive.

3. The feed composition according to claim 1, wherein the feed composition further comprises an animal feed raw material.

4. The feed composition according to claim 2, wherein the feed composition further comprises an animal feed raw material.

5. The feed composition of claim 1, wherein $R^1$ is H.

6. The feed composition of claim 5, wherein A and B are H at the same time.

7. The feed composition of claim 6, wherein Y and X are H at the same time.

8. A method of improving animal production performance, wherein the method comprises administering the feed composition of claim 1 to an animal, and wherein the improved production performance of the animal is improved weight gain or feed conversion efficiency compared to an animal not administered with the feed composition.

9. A method of improving animal production performance, wherein the method comprises administering the feed composition of claim 2 to an animal, and wherein the improved production performance of the animal is improved weight gain or feed conversion efficiency compared to an animal not administered with the feed composition.

10. A method of improving animal production performance, wherein the method comprises administering the feed composition of claim 7 to an animal, and wherein the improved production performance of the animal is improved weight gain or feed conversion efficiency compared to an animal not administered with the feed composition.

11. The feed composition of claim 5, wherein $R^2$ is $R^{2a}C(=O)-$, and $R^{2a}$ is $(A)(B)N-(CH_2)_{0-5}-$, and each of A and B is H at the same time.

12. The feed composition of claim 11, wherein each of Y and X is H at the same time.

13. The feed composition of claim 11, wherein each of Y and X is independently selected from $C_1$-$C_{20}$ alkyl or H, and each of Y and X is not H at the same time.

14. The feed composition of claim 11, wherein each of Y and X is independently selected from $C_1$-$C_4$ alkyl or $-H$, and each of Y and X is not H at the same time.

15. A method of improving animal production performance, wherein the method comprises administering the feed composition of claim 12 to an animal, and wherein the improved production performance of the animal is improved weight gain or feed conversion efficiency compared to an animal not administered with the feed composition.

* * * * *